United States Patent [19]

Munakata et al.

[11] 4,439,448

[45] Mar. 27, 1984

[54] GLUTAMINE DERIVATIVES

[75] Inventors: Hiroaki Munakata, Sagamihara; Makio Kobayashi, Machida; Kazuo Wagatsuma, Machida; Shigeru Sato, Machida; Makoto Tsurufuji, Tokyo; Hiroshi Enomoto, Kyoto, all of Japan; Shingo Matsumura, deceased, late of Kyoto, Japan, by Rumiko Matsumura, administrator

[73] Assignees: Mitsubishi Chemical Industries Ltd., Tokyo; Nippon Shinyaku Co., Ltd., Kyoto, both of Japan

[21] Appl. No.: 319,992

[22] Filed: Nov. 10, 1981

[30] Foreign Application Priority Data

Nov. 12, 1980 [JP] Japan ................................ 55-159319
Nov. 12, 1980 [JP] Japan ................................ 55-159320

[51] Int. Cl.$^3$ ............... C07C 101/447; C07C 101/453; A61K 31/24; A61K 31/195
[52] U.S. Cl. .................................. 424/309; 424/319; 560/37; 562/450
[58] Field of Search ................ 424/309, 319; 562/450; 560/37

[56] References Cited

U.S. PATENT DOCUMENTS

| | | | |
|---|---|---|---|
| 3,551,419 | 12/1970 | Re ........................................ | 424/319 |
| 3,739,013 | 6/1973 | Picciola ............................... | 562/450 |
| 4,177,109 | 12/1979 | Tohyama ............................ | 562/450 |
| 4,180,588 | 12/1979 | Mori .................................... | 424/319 |

*Primary Examiner*—Michael L. Shippen
*Attorney, Agent, or Firm*—Oblon, Fisher, Spivak, McClelland & Maier

[57] ABSTRACT

Glutamine derivatives and non-toxic salts thereof have been found to have immunomodulating activities.

7 Claims, 23 Drawing Figures

GLUTAMINE DERIVATIVES

BACKGROUND OF THE INVENTION

This invention relates to novel glutamine derivatives having immunomodulating activities.

We previously found out that certain glutamine derivatives had immunosuppressive activities (Japanese Laid-Open Specifications Nos. 36428/1980, 36453/1980 and 36454/1980). Upon further earnest investigation, we have now found out that certain novel glutamine derivatives possess immunomodulating activities and accomplished this invention.

SUMMARY OF THE INVENTION

Thus, the present invention resides in glutamine derivatives of the formula:

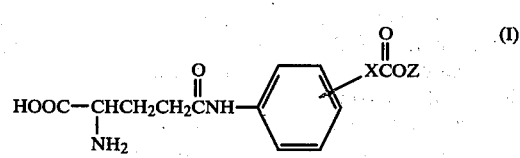
(I)

wherein X is (i) an alkylene of the formula: $-(CH_2)_n-$ where n is an integer of 1 to 4, or vinylene, or (ii) a group of the formula:

where $R^1$ and $R^2$ may be the same or different and are hydrogen or a lower alkyl with the proviso that at least one of $R^1$ and $R^2$ is a lower alkyl; and Z is hydrogen or a lower alkyl and non-toxic salts thereof.

The term "immunomodulating activity" used herein is intended to encompass both of immunosuppressive activity and immunostimulating activity.

DETAILED DESCRIPTION OF PREFERRED EMBODIMENTS

Figure 1:
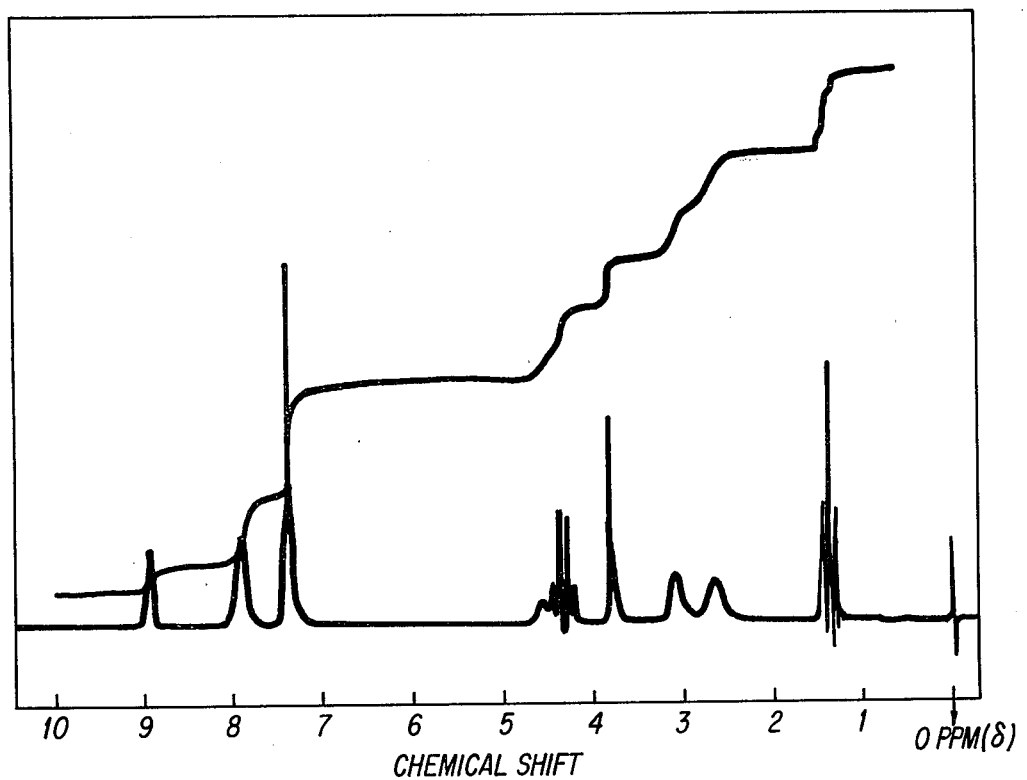
FIGS. 1, 4, 8, 13, 15, 17 and 20 are charts showing the NMR spectra of products obtained in examples.

The compounds according to this invention are those of the foregoing formula (I) and non-toxic salts thereof. These compounds include, for example, glutamine derivatives of the formula:

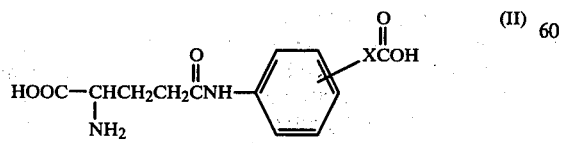
(II)

where X is as defined in Formula (I) and non-toxic salts thereof, as well as glutamine derivatives of the formula:

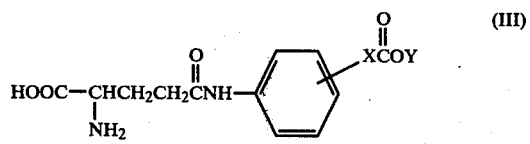
(III)

where X is as defined in Formula (I) and Y is a lower alkyl, and non-toxic salts thereof.

The lower alkyl for group Y in Formula (III) is an alkyl having 1 to 4 carbon atoms which includes methyl, ethyl, propyl, butyl, isopropyl, sec-butyl and tert-butyl.

In Formula (I), the glutamine moiety may be any of L-, DL- and D-isomers.

The glutamine derivatives of Formula (I) include, for example:

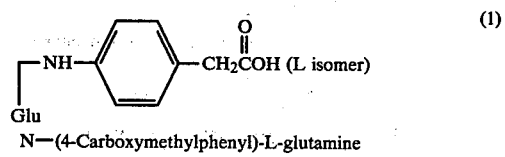
(1)

N—(4-Carboxymethylphenyl)-L-glutamine

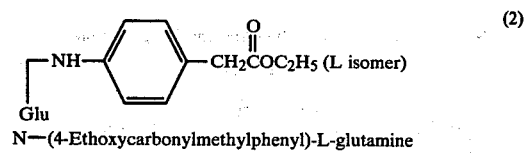
(2)

N—(4-Ethoxycarbonylmethylphenyl)-L-glutamine

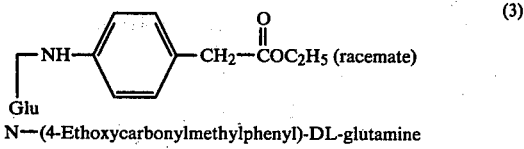
(3)

N—(4-Ethoxycarbonylmethylphenyl)-DL-glutamine

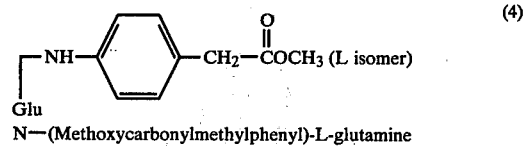
(4)

N—(Methoxycarbonylmethylphenyl)-L-glutamine

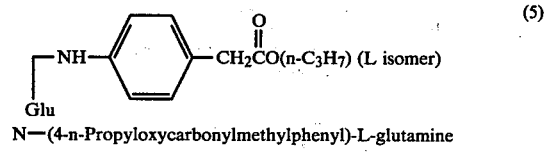
(5)

N—(4-n-Propyloxycarbonylmethylphenyl)-L-glutamine

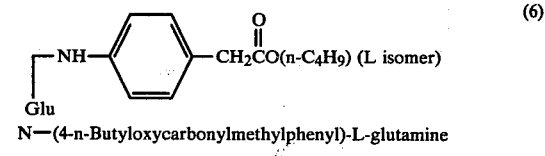
(6)

N—(4-n-Butyloxycarbonylmethylphenyl)-L-glutamine

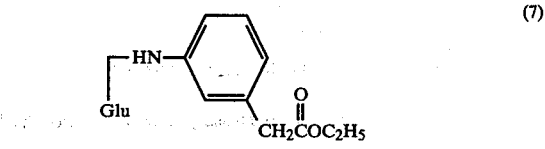
(7)

N—(3-Ethoxycarbonylmethylphenyl)-L-glutamine

-continued (8) 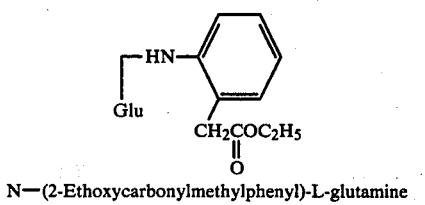
N—(2-Ethoxycarbonylmethylphenyl)-L-glutamine (9) 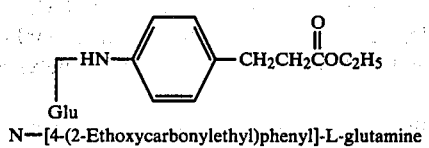
N—[4-(2-Ethoxycarbonylethyl)phenyl]-L-glutamine

(10) 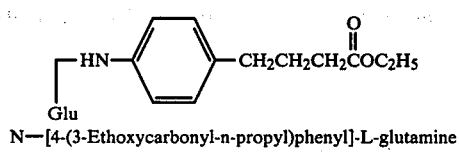
N—[4-(3-Ethoxycarbonyl-n-propyl)phenyl]-L-glutamine

(11) 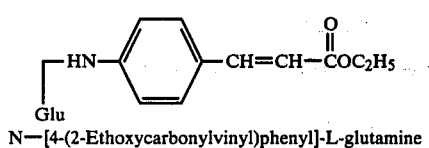
N—[4-(2-Ethoxycarbonylvinyl)phenyl]-L-glutamine

(12) 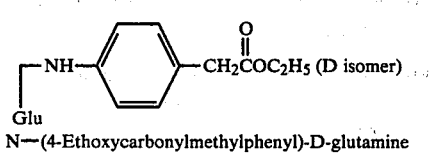
N—(4-Ethoxycarbonylmethylphenyl)-D-glutamine

(13) 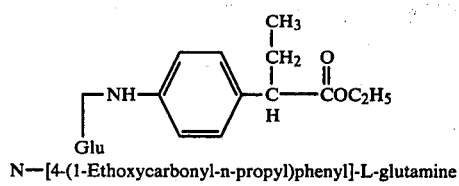
N—[4-(1-Ethoxycarbonyl-n-propyl)phenyl]-L-glutamine

(14) 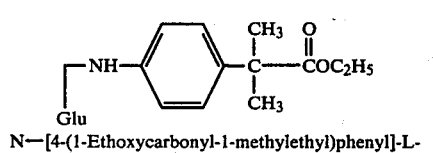
N—[4-(1-Ethoxycarbonyl-1-methylethyl)phenyl]-L-glutamine

(15) 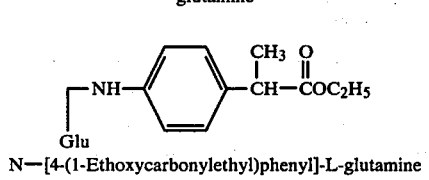
N—[4-(1-Ethoxycarbonylethyl)phenyl]-L-glutamine

(16) 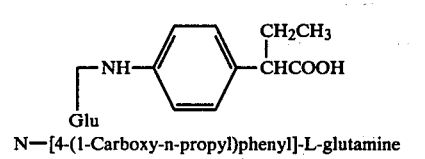
N—[4-(1-Carboxy-n-propyl)phenyl]-L-glutamine

In the above structural formulas, the glutamic acid residue

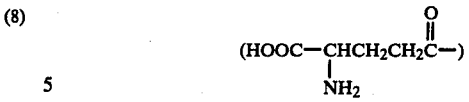

is abbreviated as "Glu" for brevity.

Also for brevity, the individual compounds may hereinafter be expressed by the above number, for example, as "Compound (1)".

Non-toxic salts of these L-, D- or DL-glutamine derivatives are pharmaceutically acceptable salts which include, for example, salts with an inorganic base such as an alkali or alkaline earth metal, e.g., sodium, potassium, calcium, etc.; salts with an organic base such as procaine, N,N'-dibenzylethylenediamine, etc.; acid addition salts such as hydrochloride, sulfate, fumarate, maleate, formate, etc.; and the like.

The compounds according to this invention may be prepared in the following manner. For convenience, the preparation of the compounds of this invention will be described in two groups of the compounds of Formula (II) (hereinafter referred to as "carboxylic acids of this invention") and those of Formula (III) (hereinafter referred to as "esters of this invention").

The carboxylic acids of this invention may be prepared by various synthetic methods. For example, they may readily be prepared from an appropriate ester of this invention by a conventional ester hydrolysis procedure.

The esters of this invention may be prepared in any conventional manner. For example, they may be obtained by the reaction of amino-protected glutamic acid anhydride with an aniline derivative of the formula:

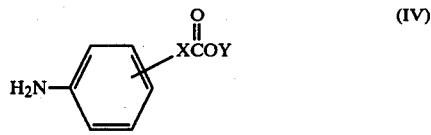 (IV)

where X and Y are as defined in Formula (III), followed by elimination of the amino-protecting group.

Another process for the preparation of the esters of this invention comprises reacting glutamic acid in which both the α-carboxyl and α-amino groups are protected with an aniline derivative of Formula (IV) in the presence of an activating agent or reacting a reactive derivative at the γ-carboxyl group of such α-carboxyl- and α-amino-protected glutamic acid with the foregoing aniline derivative, followed by elimination of the amino- and carboxyl-protecting groups.

Any activating agent or reactive derivative which can be used in the conventional peptide synthesis may be employed. Illustrative thereof are such activating agents as dicyclohexylcarbodiimide, carboxyldiimidazole, etc., and such reactive derivatives as mixed acid anhydrides, activated esters, etc.

The protective group for amino may be any group which can be eliminated later under mild conditions and which is used in the conventional peptide synthesis. Examples of such group include benzyloxycarbonyl group which is eliminable with hydrogen bromide or by catalytic reduction, phthalyl group eliminable with hydrazine, tert-butoxycarbonyl and formyl groups which are eliminable under weakly acidic conditions, and the like.

The protective group for carboxyl includes esters with benzyl or its derivative which is eliminated by catalytic reduction, tert-butyl esters which are stable to alkalis and eliminated by hydrolysis with an acid.

By way of example, N-(4-ethoxycarbonylmethylphenyl)-L-glutamine can be prepared by either of the two synthetic routes which are shown by the following reaction scheme.

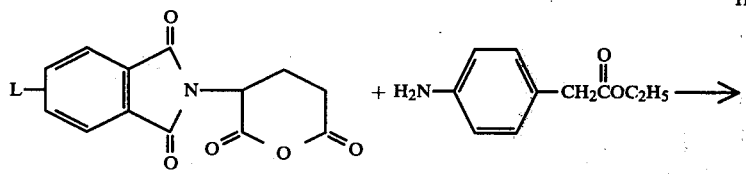

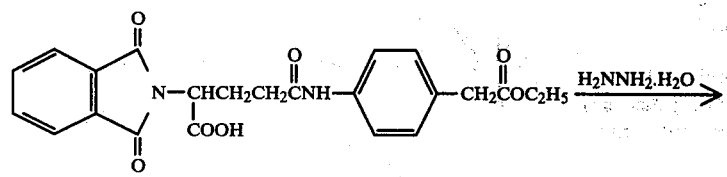

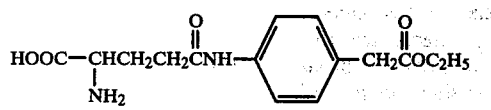

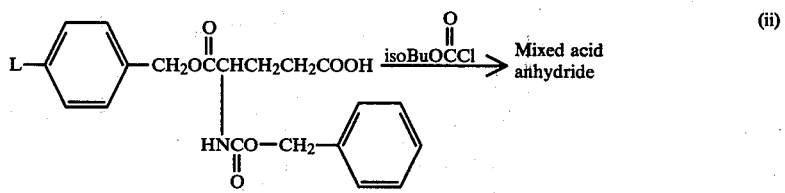

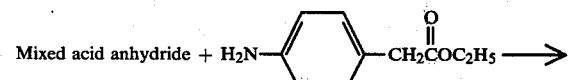

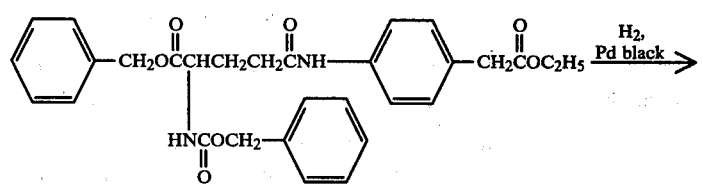

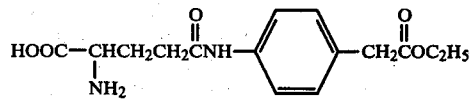

Similarly, N-[4-(1-ethoxycarbonyl-n-propyl)phenyl]-L-glutamine can be prepared, for example, by the following synthetic route.

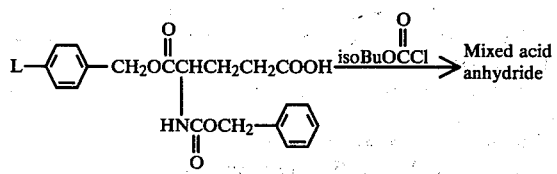

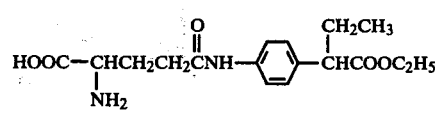

The aniline derivatives of the foregoing Formula (IV) which are used as starting materials can be prepared by various synthetic routes. For reference, examples of such synthetic routes are shown below in two groups with respect to X.

(1) In the case where X is an alkylene of the formula: $-(CH_2)_n-$ or vinylene:

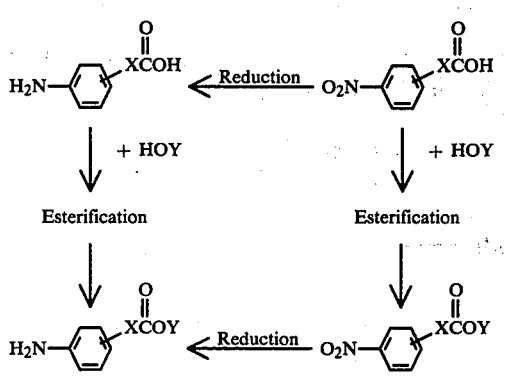

The reduction may be performed by catalytic hydrogenation using palladium, palladium black or palladium on charcoal. Alternatively, reduction with iron powder/$NH_4Cl$ or the like may be applied.

The esterification may be conducted by heating along with the starting alcohol in the presence of hydrochloric, sulfuric or p-toluenesulfonic acid, if necessary, followed by azeotropic dehydration in the presence of an azeotropic agent, thereby readily providing the desired ester.

The compound

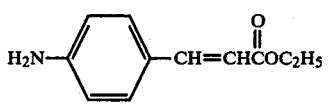

can readily be obtained by reduction of

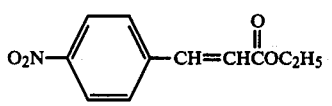

with iron powder/$NH_4Cl$.

(2) In the case where X is a group of the formula:

$$-\overset{R^2}{\underset{R^1}{C}}-:$$

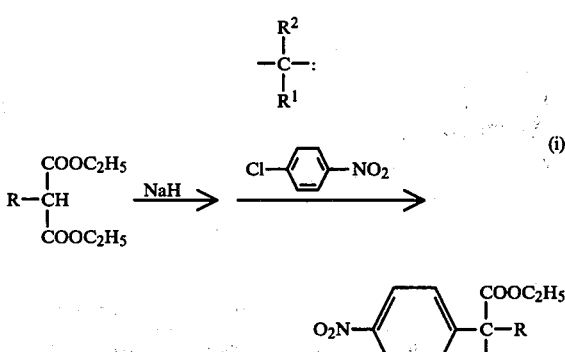

(where R is methyl or ethyl)

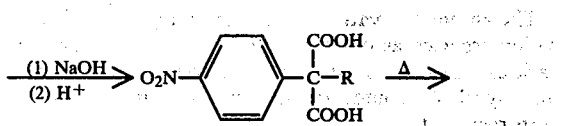

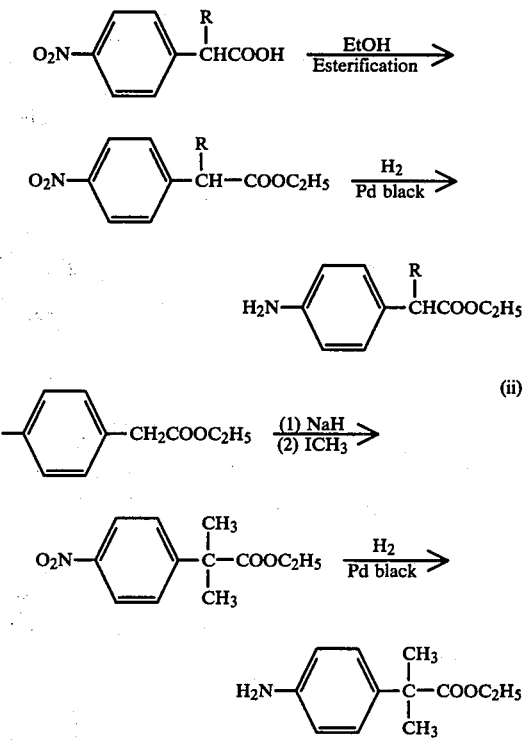

A diethyl 2-alkyl-2-(4-nitrophenyl)malonate which is the starting material in the above Process (i) can be obtained by reacting a 2-alkyl malonate with a strong base such as sodium hydride in N,N-dimethylformamide and then with p-halonitrobenzene.

Hydrolysis of the resulting ester may be effected by reaction with sodium hydroxide, potassium hydroxide or the like in water or an alcohol (methanol, ethanol, etc.) or a mixture thereof.

An α-alkyl-nitrophenylacetic acid can be obtained by heating a diethyl 2-alkyl-2-(4-nitriophenyl)malonate along with excess sodium hydroxide or potassium hydroxide in water or an alcohol (methanol, ethanol, etc.) or a mixture thereof, or by heating a 2-alkyl-2-(4-nitrophenyl)malonic acid along with a suitable acid such as hydrochloric, sulfuric or p-toluenesulfonic acid in a suitable solvent such as an alcohol (methanol, ethanol, etc.), benzene, or toluene.

The subsequent esterification may be performed by heating with ethanol in the presence of hydrochloric, sulfuric or p-toluenesulfonic acid.

The reduction of nitro group in the next step may be effected either by catalytic hydrogenation using palladium or palladium black or reduction with iron powder/$NH_4Cl$.

Ethyl 2-methyl-2-nitrophenylpropionate which is the starting material in the above Process (ii) can be obtained by reacting ethyl nitrophenylacetate with a strong base such as sodium hydride in N,N-dimethylformamide and then with excess methyl iodide.

The subsequent reduction of nitro group may be effected either by catalytic hydrogenation using palladium or palladium black or by reduction with iron powder/$NH_4Cl$.

The desired glutamine derivatives obtained by these processes may be purified by means of recrystallization, ion-exchange treatment, chromatography, activated charcoal treatment or the like, according to the conventional practice in organic chemistry.

The compounds according to this invention are valuable as immunomodulating agent for use in therapy and prevention of various diseases caused by immunoreactions.

Although pharmaceutical compositions for immunomodulation which contain at least one compound of this invention may consist essentially of one or more of such compounds, the compounds of this invention are generally used, according to the conventional manner, in admixture with one or more auxiliaries and/or pharmaceutically acceptable carriers, in the form of conventional pharmaceutical preparations, for example, tablets, fine granules, powders, granules, capsules, syrups for oral administration, and ointments, liniments, suppositories, injections for parenteral administration.

The formulations of these preparations vary depending on the administration route, administration plan and the like.

The dosage may vary depending on the age, condition, weight and degree of symptoms of the patient, the type of concomitant treatment, if any, the frequency of treatment, the nature of the desired effect and the like.

The daily therapeutic dose is generally in the range of 0.1 to 100 mg/kg for parenteral administration and in the range of 1 to 1,000 mg/kg for oral administration.

The pharmaceutical compositions for immunomodulation which comprises at least one compound of this invention may further contain, for example, one or more other immunosuppressive or immunostimulating agents or may be used along with such agents.

The compounds of this invention have low toxicity and are useful as immunomodulation agents for use in therapy and prevention of various diseases caused by immunoreactions.

The pharmaceutical compositions for immunomodulation which comprise one or more compounds of this invention may be used in therapy, for example, of the following diseases: autoimmune diseases such as rheumatoid arthritis, systemic lupus erythematodes (SLE), collagent disease, etc.; allergic diseases such as asthma, etc.; cancer; bacterial infectious diseases and the like.

A mutagenicity test of Compound (2) (~100 μg/plate) using six strains as stipulated in the Labor Safety and Hygiene Law in Japan as test strains showed that it was negative in mutagenicity, within the range of such experiment.

The present invention will be further illustrated by the following preparation and examples. It should be understood, however, that the examples are given only for the purpose of illustration and not intended to limit the present invention in any way.

PREPARATION 1

In 15% hydrogen chloride-ethanol, p-aminophenol was heated under reflux. After removal of ethanol by distillation, the residue was extracted with ethyl acetate and the extract was washed successively with water, saturated sodium bicarbonate solution and water and dried. The ethyl acetate was then distilled off to give p-aminophenylacetic acid ethyl ester.

In a similar manner, the methyl, n-propyl and n-butyl esters were obtained from hydrogen chloride in the appropriate alcohols.

In 15% hydrogen chloride-ethanol, m- or o-nitrophenylacetic acid was ethyl-esterified and the resulting ethyl ester was hydrogenated with palladium catalyst in ethanol to give m- or o-aminophenylacetic acid ethyl ester.

In a similar manner, ethyl 4-(p-aminophenyl)butyrate was also obtained.

Likewise, p-nitrocinnamic acid was subjected to ethyl esterification and then to hydrogenation with palladium catalyst to give ethyl 3-(p-aminophenyl)propionate. When the hydrogenation was effected by heating under reflux in iron powder-ammonium chloride-water-methanol, the resulting product was ethyl p-aminocinnamate.

EXAMPLE 1

N-(4-Ethoxycarbonylmethylphenyl)-L-glutamine: Compound (1)

(a) To a mixture of 250 ml of tetrahydrofuran and 250 ml of N,N-dimethylformamide were added 74.28 g (0.2 mole) of N-carbobenzoxy-L-glutamic acid α-benzyl ester and 28 ml (0.2 mole) of triethylamine. Under stirring with ice cooling, 26.4 ml (0.2 mole) of isobutyl chlorocarbonate was then added dropwise and stirred for 15 minutes. Thereafter, a solution of 35.84 g (0.2 mole) of ethyl p-aminophenylacetate in 50 ml of tetrahydrofuran and 50 ml of N,N-dimethylformamide was added and the mixture was stirred for 30 minutes under ice cooling and then for 8 hours at room temperature.

The reaction solvent was distilled off in vacuo and to the residue were added 1,200 ml of ethyl acetate and 200 ml of water. The water layer was removed. The ethyl acetate layer was washed successively with 2 N hydrochloric acid, saturated sodium bicarbonate solution and saturated sodium chloride solution and dried over anhydrous magnesium sulfate. After the ethyl acetate was distilled off in vacuo, the residue was recrystallized from ethyl acetate-n-hexane to give an intermediate. Yield: 96.16 g (90.7%).

To 53.26 g (0.1 mole) of the intermediate obtained above were added 1,600 ml of ethanol and 600 ml of water and heated until a solution was formed. Thereafter 0.5 g of palladium black was added and the mixture was subjected to hydrogenation at atmospheric pressure to eliminate the protective group.

Palladium was filtered off while hot and the filtrate was treated with activated charcoal and concentrated. The precipitated crystals were then collected by filtration, washed with ice water and dried to give 28.57 g (93% yield) of N-(4-ethoxycarbonylmethylphenyl)-L-glutamine, m.p. 179.8°–180.5° C.

| Elementary analysis (wt. %) | C | H | N |
|---|---|---|---|
| Calc. for $C_{15}H_{20}N_2O_5$: | 58.43 | 6.54 | 9.09 |
| Found: | 58.59 | 6.60 | 9.23 |

$[\alpha]_D^{25} = +29.5°$ (c=1, 2 N HCl)

Figure 2:
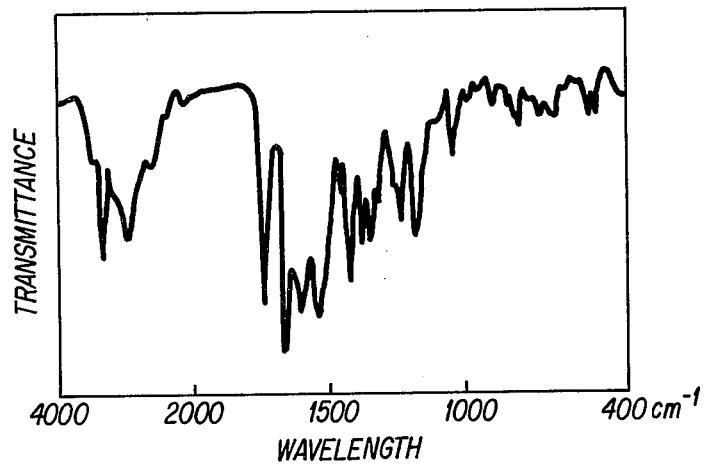
FIGS. 2, 3, 5, 6, 7, 9–12, 14, 16, 18, 19 and 21–23 are charts showing the IR spectra of products obtained in examples.

The NMR and IR spectra of the product are shown in FIGS. 1 and 2, respectively.

The NMR spectrum was measured at room temperature in trifluoroacetic acid using tetramethylsilane as a reference, while the IR spectrum was measured in potassium bromide. (The measurement of these spectra was made in the same manner also in the following examples.)

(b) To 100 ml of tetrahydrofuran were added 7.43 g (0.02 mole) of N-carbobenzoxy-L-glutamic acid α-benzyl ester and 3.58 g (0.02 mole) of ethyl p-aminophenylacetate and under ice cooling and stirring 2.2 ml (0.024 mole) of phosphorus oxychloride was added and stirred for 15 minutes. A solution of 6.4 ml (0.046 mole) of triethylamine in 30 ml of tetrahydrofuran was added dropwise over 25 minutes under ice cooling and the mixture was stirred for 1 hour under cooling and for 3 hours at room temperature.

After the tetrahydrofuran was distilled off in vacuo, ethyl acetate was added to the residue. The ethyl acetate solution was then washed successively with water, 2 N hydrochloric acid, saturated sodium bicarbonate solution and saturated sodium chloride solution and dried over anhydrous magnesium sulfate. Then the ethyl acetate was distilled off in vacuo and the residue was recrystallized from ethyl acetate-n-hexane to give 6.5 g (63% yield) of an intermediate.

The intermediate was subjected to elimination of the protective group as described in (a) to give 3.4 g (90% yield) of N-(4-ethoxycarbonylmethylphenyl)-L-glutamine.

(c) To 200 ml of tetrahydrofuran was added 5.18 g (0.02 mole) of N-phthalyl-L-glutamic acid anhydride and the mixture was heated under reflux for 3 hours. The tetrahydrofuran solvent was then distilled off in vacuo.

To the residue were added 200 ml of ethanol and 1.33 ml (0.022 mole) of 80 wt. % hydrazine hydrate and the mixture was stirred for 1 hour at room temperature and then heated under reflux for 3 hours. After the ethanol was distilled off in vacuo, 300 ml of 2 N hydrochloric acid was added to the residue and stirred. The insoluble matters were then removed and the solution was neutralized with conc. aqueous ammonia. The precipitated crystals were collected by filtration, washed with ice water and dried to give 3.4 g (55% yield) of N-(4-ethoxycarbonylmethylphenyl)-L-glutamine, m.p. 179.4°–180.0° C.

| Elementary analysis (wt. %) | C | H | N |
|---|---|---|---|
| Calc. for $C_{15}H_{20}N_2O_5$: | 58.43 | 6.54 | 9.09 |
| Found: | 58.20 | 6.67 | 9.01 |

$[\alpha]_D^{26} = +28.5°$ (c=1 2 N HCl)

Figure 3:
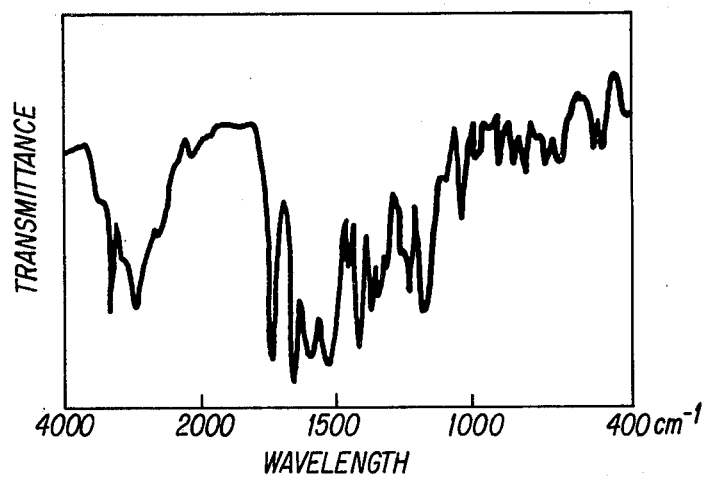

The IR spectrum of the product is shown in FIG. 3.

EXAMPLE 2

N-(4-Carboxymethylphenyl)-L-glutamine: Compound (2)

A solution of 0.62 g (0.0094 mole) of 85% potassium hydroxide in 10 ml of water was added to a suspension of 1.45 g (0.0047 mole) of N-(4-ethoxycarbonylmethylphenyl)-L-glutamine in 20 ml of water and the mixture was stirred for 4 hours at room temperature.

Under ice cooling, the reaction mixture was acidified to pH 3 with 2 N hydrochloric acid and the precipitated crystals were collected by filtration, washed with ice water and dried to give 1.21 g (92% yield) of N-(4-carboxymethylphenyl)-L-glutamine, m.p. 197.7°–199.6° C.

| Elementary analysis (wt. %) | C | H | N |
|---|---|---|---|
| Calc. for $C_{13}H_{16}N_2O_5$: | 55.71 | 5.75 | 10.00 |
| Found: | 55.69 | 5.58 | 9.75 |

$[\alpha]_D^{26} = +16.6$ (c=1 0.5 N sodium carbonate)

Figure 4:
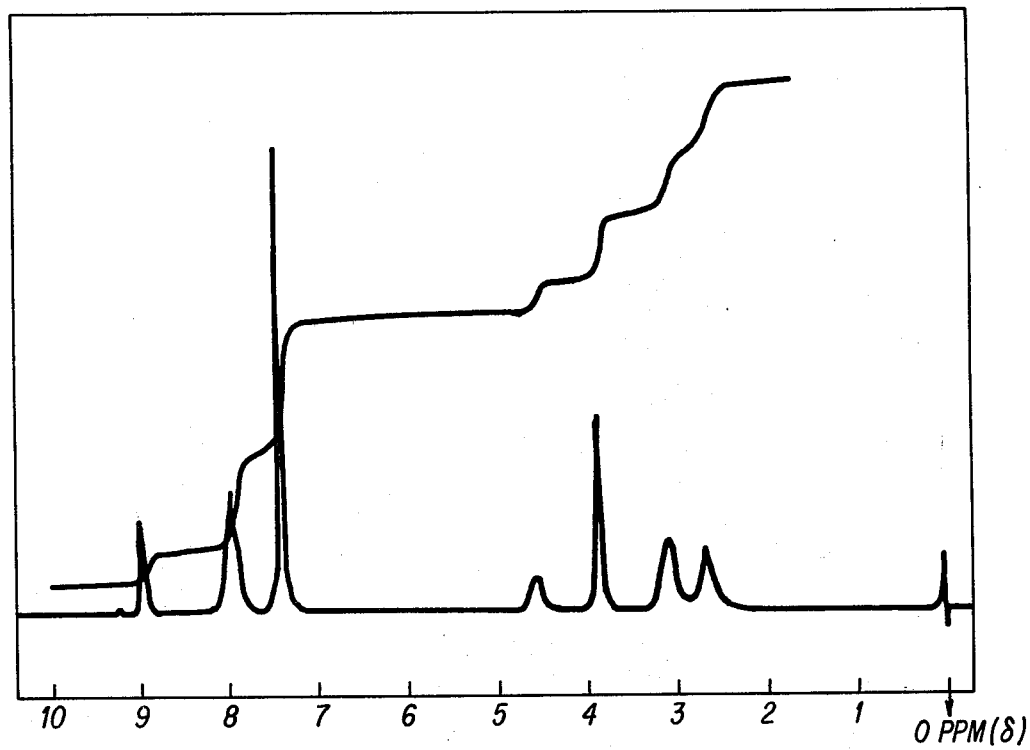
Figure 5:
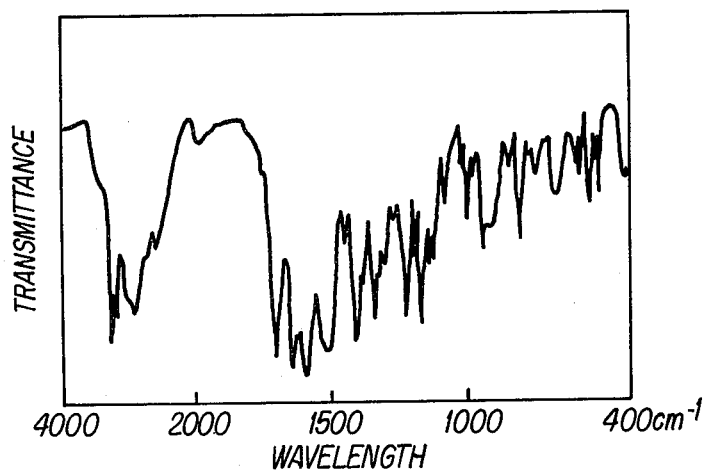

The NMR and IR spectra of the product are shown in FIGS. 4 and 5, respectively.

EXAMPLE 3

N-(4-Methoxycarbonylmethylphenyl)-L-glutamine: Compound (3)

Following the procedure described in (a) of Example 1, 11.14 g (0.03 mole) of N-carbobenzoxy-L-glutamic acid α-benzyl ester was reacted with 4.96 g (0.03 mole) of methyl p-aminophenylacetate to give 13.38 g (88% yield) of an intermediate.

The intermediate was dissolved in 500 ml of tetrahydrofuran, 200 ml of methanol and 100 ml of water. To the solution was added 0.5 g of palladium black and the mixture was subjected to hydrogenation at atmospheric pressure to give 6.09 g (79% yield) of N-(4-methoxycarbonylmethylphenyl)-L-glutamine, m.p. 183.3°–184.2° C.

| Elementary analysis (wt. %) | C | H | N |
|---|---|---|---|
| Calc. for $C_{14}H_{18}N_2O_5$: | 57.13 | 6.16 | 9.52 |
| Found: | 57.10 | 6.05 | 9.74 |

$[\alpha]_D^{25} = +29.2°$ (c=1 2 N HCl)

Figure 6:
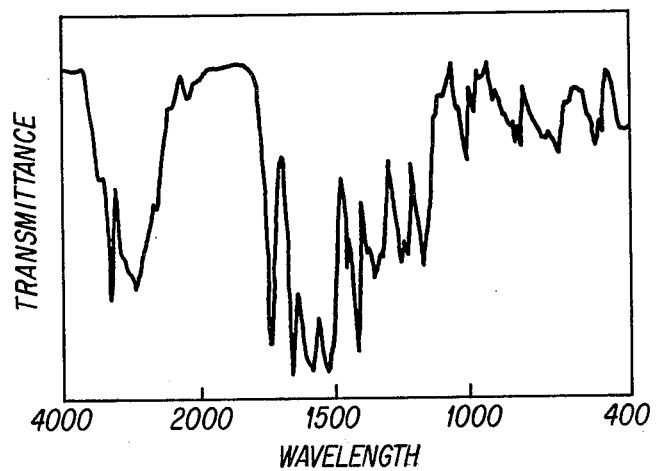

The IR spectrum of the product is shown in FIG. 6.

EXAMPLE 4

N-(4-n-Propyloxycarbonylmethylphenyl)-L-glutamine: Compound (4)

Following the procedure described in (a) of Example 1, 11.43 g (0.03 mole) of N-carbobenzoxy-L-glutamic acid α-benzyl ester was reacted with 5.8 g (0.03 mole) of n-propyl p-aminophenylacetate to give 14.05 (88% yield) of an intermediate.

The intermediate was dissolved in 500 ml of tetrahydrofuran, 200 ml of methanol and 100 ml of water. To the solution was added 0.5 g of palladium black and the mixture was subjected to hydrogenation at atmospheric pressure to give 6.09 g (79% yield) of N-(4-n-propyloxycarbonylmethylphenyl)-L-glutamine, m.p. 177.6°–178.9° C.

| Elementary analysis (wt. %) | C | H | N |
|---|---|---|---|
| Calc. for $C_{16}H_{22}N_2O_5$: | 59.61 | 6.88 | 8.69 |
| Found: | 59.88 | 6.99 | 8.52 |

$[\alpha]_D^{25} = +22.8°$ (c=1 2 N HCl)

Figure 7:
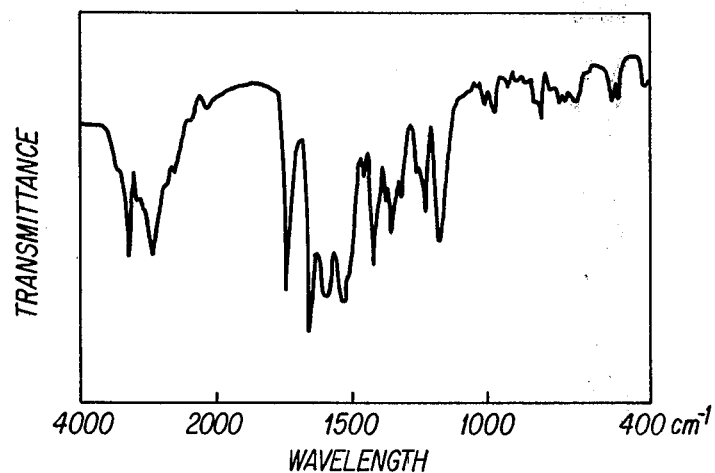

The IR spectrum of the product is shown in FIG. 7.

EXAMPLE 5

N-(4-n-Butyloxycarbonylmethylphenyl)-L-glutamine: Compound (5)

Following the procedure described in (a) of Example 1, 11.14 g (0.03 mole) of N-carbobenzoxy-L-glutamic acid α-benzyl ester was reacted with 6.21 g (0.03 mole) of n-butyl p-aminophenylacetate to give 15.0 g (92% yield) of an intermediate.

The intermediate was dissolved in 500 ml of tetrahydrofuran, 200 ml of methanol and 100 ml of water. To the solution was added 0.5 g of palladium black and the mixture was subjected to hydrogenation at atmospheric pressure to give 5.72 g (62% yield) of N-(4-n-butyloxycarbonylmethylphenyl)-L-glutamine, m.p. 177.0°–179.2° C.

| Elementary analysis (wt. %) | C | H | N |
| --- | --- | --- | --- |
| Calc. for $C_{17}H_{24}N_2O_5$: | 60.70 | 7.19 | 8.23 |
| Found: | 60.61 | 7.11 | 8.44 |

$[\alpha]_D^{25} = +25.4°$ (c=1 2 N HCl)

Figure 8:
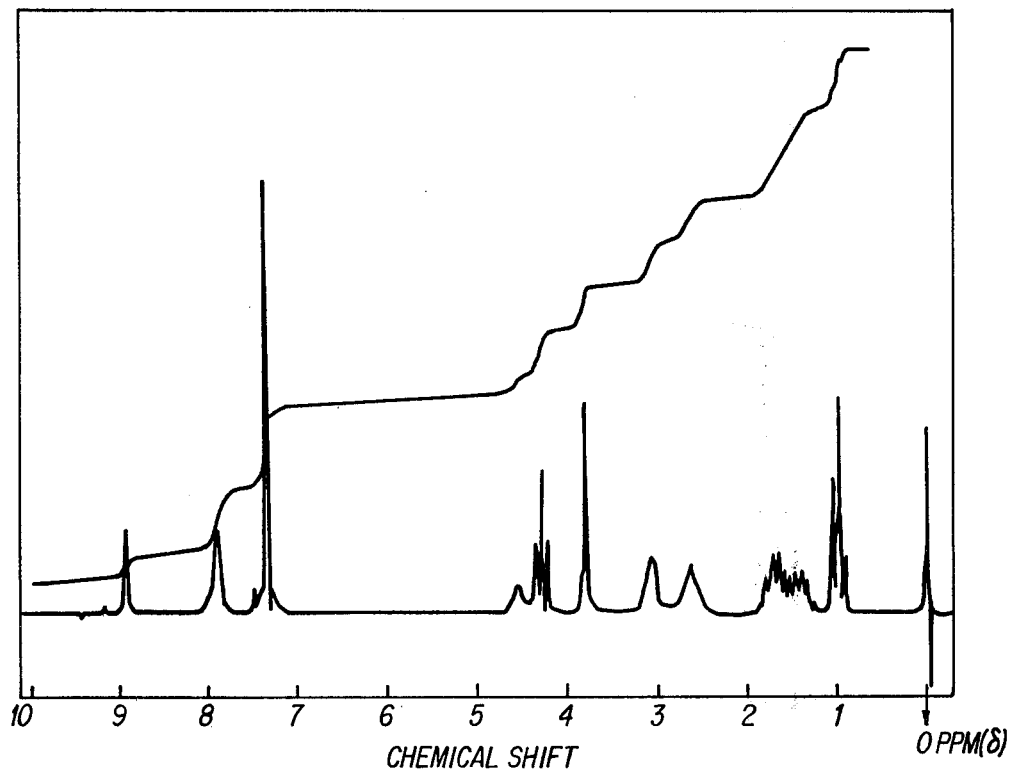
Figure 9:
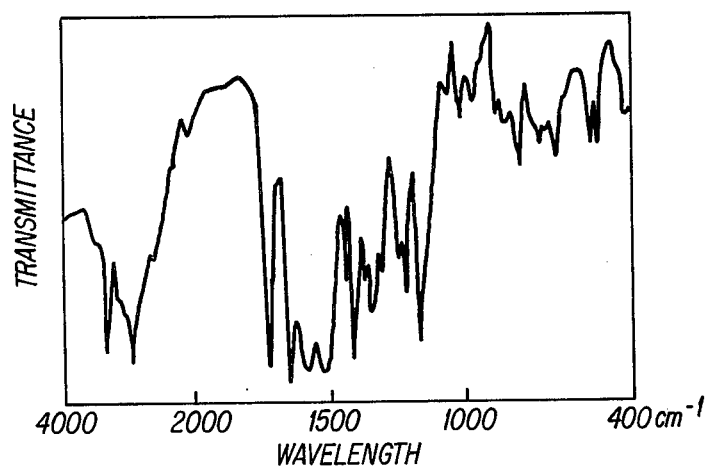

The NMR and IR spectra of the product are shown in FIGS. 8 and 9, respectively.

EXAMPLE 6

N-(3-Ethoxycarbonylmethylphenyl)-L-glutamine: Compound (6)

Following the procedure described in (a) of Example 1, 11.14 g (0.03 mole) of N-carbobenzoxy-L-glutamic acid α-benzyl ester was reacted with 4.96 g (0.03 mole) of ethyl m-aminophenylacetate to give 12.95 g (81% yield) of an intermediate.

The intermediate was dissolved in 500 ml of tetrahydrofuran, 200 ml of ethanol and 100 ml of water. To the solution was added 0.3 g of palladium black and the mixture was subjected to hydrogenation at atmospheric pressure to give 6.58 g (89% yield) of N-(3-ethoxycarbonylmethylphenyl)-L-glutamine, m.p. 175.5°–176.2° C.

| Elementary analysis (wt. %) | C | H | N |
| --- | --- | --- | --- |
| Calc. for $C_{15}H_{20}N_2O_5$: | 58.43 | 6.54 | 9.09 |
| Found: | 58.41 | 6.46 | 9.01 |

$[\alpha]_D^{25} = +26.4°$ (c=1 2 N HCl)

Figure 10:
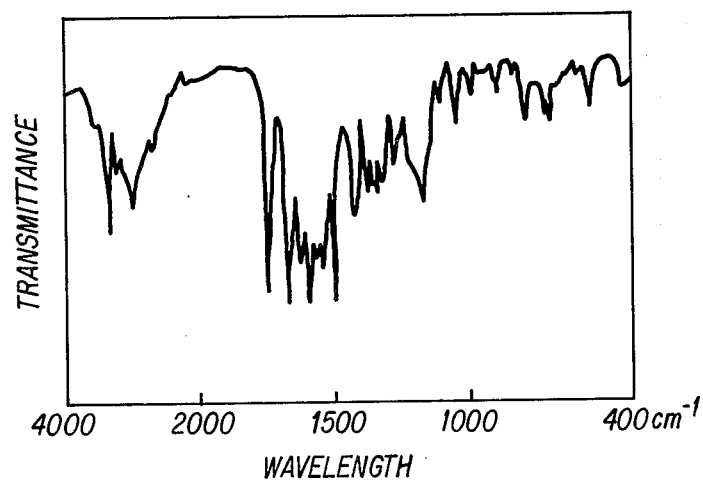

The IR spectrum of the product is shown in FIG. 10.

EXAMPLE 7

N-(2-Ethoxycarbonylmethylphenyl)-L-glutamine: Compound (7)

Following the procedure described in (a) of Example 1, 11.14 g (0.03 mole) of N-carbobenzoxy-L-glutamic acid α-benzyl ester was reacted with 4.96 g (0.03 mole) of ethyl o-aminophenylacetate to give 14.19 g (88% yield) of an intermediate.

The intermediate was dissolved in 200 ml of tetrahydrofuran, 200 ml of ethanol and 100 ml of water. To the solution was added 0.3 g of palladium black and the mixture was subjected to hydrogenation at atmospheric pressure to give 6.85 g (84% yield) of N-(2-ethoxycarbonylmethylphenyl)-L-glutamine, m.p. 171.2°–171.8° C.

| Elementary analysis (wt. %) | C | H | N |
| --- | --- | --- | --- |
| Calc. for $C_{15}H_{20}N_2O_5$: | 58.43 | 6.54 | 9.09 |
| Found: | 58.16 | 6.31 | 8.99 |

$[\alpha]_D^{25} = +21.6°$ (c=1 2 N HCl)

Figure 11:
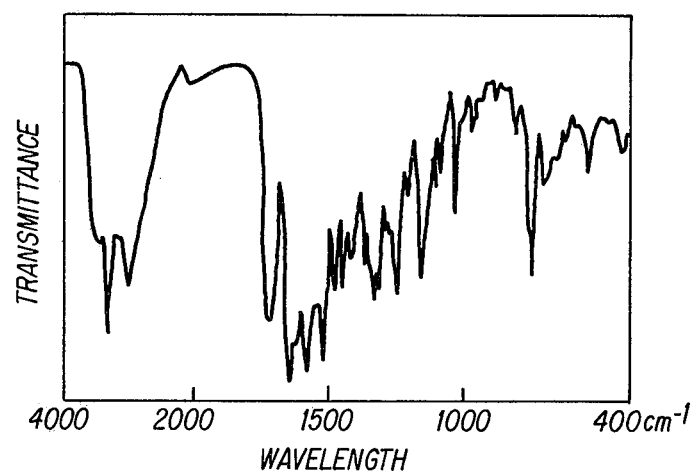

The IR spectrum of the product is shown in FIG. 11.

EXAMPLE 8

N-[4-(2-Ethoxycarbonylethyl)phenyl]-L-glutamine: Compound (8)

Following the procedure described in (a) of Example 1, 11.14 g (0.03 mole) of N-carbobenzoxy-L-glutamic acid α-benzyl ester was reacted with 5.8 g (0.03 mole) of ethyl p-aminophenylpropionate to give 12.8 g (78% yield) of an intermediate.

The intermediate was dissolved in 200 ml of tetrahydrofuran, 200 ml of ethanol and 100 ml of water. To the solution was added 0.3 g of palladium black and the mixture was subjected to hydrogenation at atmospheric pressure to give 7.09 g (92% yield) of N-[4-(2-ethoxycarbonylethyl)phenyl]-L-glutamine, m.p. 179.5°–180.6° C.

| Elementary analysis (wt. %) | C | H | N |
| --- | --- | --- | --- |
| Calc. for $C_{16}H_{22}N_2O_5$: | 59.71 | 6.88 | 8.69 |
| Found: | 59.63 | 6.68 | 8.62 |

$[\alpha]_D^{25} = +25.8°$ (c=1 2 N HCl)

Figure 12:
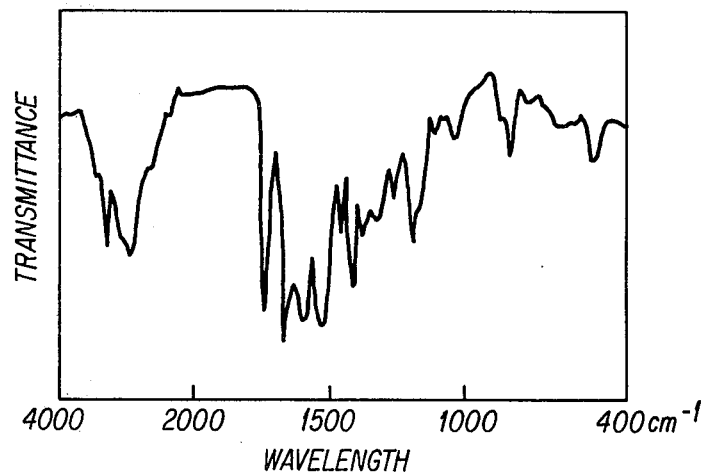

The IR spectrum of the product is shown in FIG. 12.

EXAMPLE 9

N-[4-(3-Ethoxycarbonyl-n-propyl)phenyl]-L-glutamine: Compound (9)

Following the procedure described in (a) of Example 1, 11.14 g (0.03 mole) of N-carbobenzoxy-L-glutamic acid α-benzyl ester was reacted with 6.22 g (0.03 mole) of ethyl p-aminophenylbutyrate to give 14.7 g (87% yield) of an intermediate.

The intermediate was dissolved in 200 ml of tetrahydrofuran, 200 ml of ethanol and 100 ml of water. To the solution was added 0.3 g of palladium black and the mixture was subjected to hydrogenation at atmospheric pressure to give 8.6 g (98% yield) of N-[4-(3-ethoxycarbonyl-n-propyl)phenyl]-L-glutamine, m.p. 179.0°–180.1° C.

| Elementary analysis (wt. %) | C | H | N |
| --- | --- | --- | --- |
| Calc. for $C_{17}H_{24}N_2O_5$: | 60.70 | 7.19 | 8.33 |
| Found: | 60.37 | 6.99 | 8.55 |

$[\alpha]_D^{25} = +24.0°$ (c=1 2 N HCl)

Figure 13:
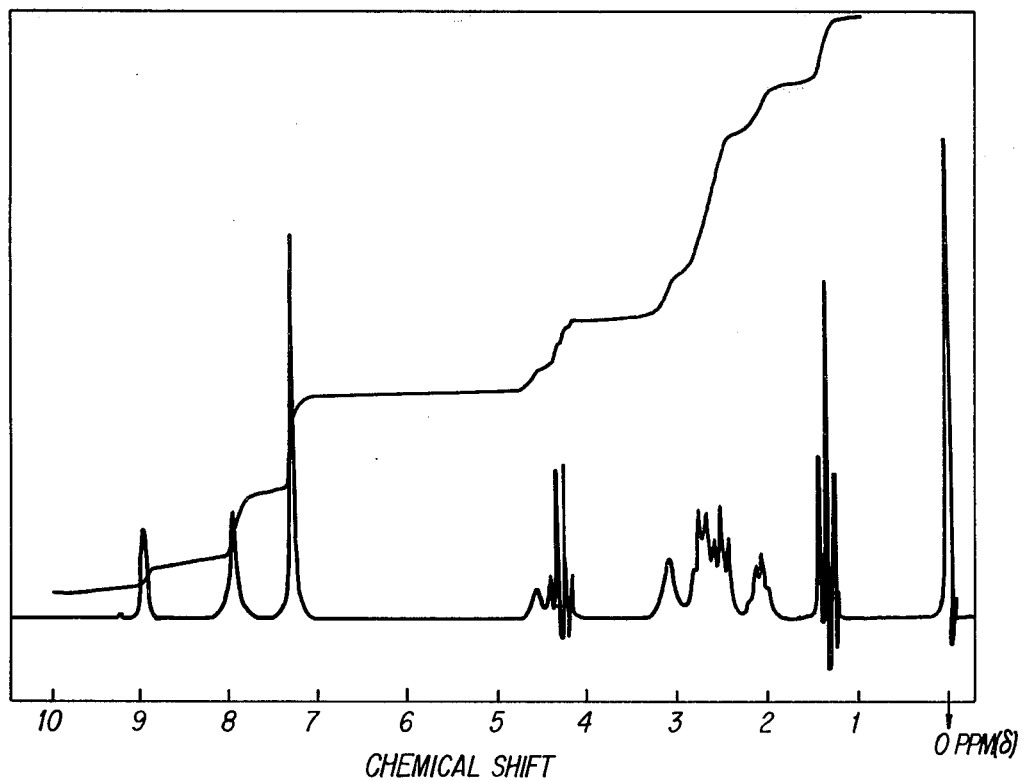
Figure 14:
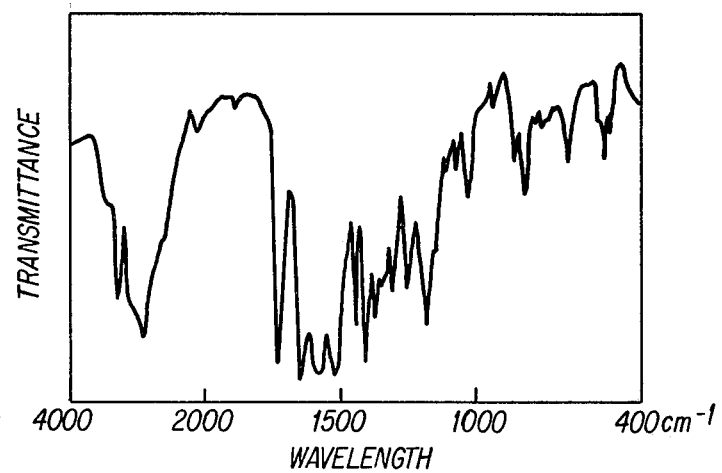

The NMR and IR spectra of the product are shown in FIGS. 13 and 14, respectively.

EXAMPLE 10

N-[4-(2-Ethoxycarbonylvinyl)phenyl]-L-glutamine: Compound (10)

Following the procedure described in (c) of Example 1, 25.9 g (0.1 mole) of N-phthalyl-L-glutamic acid anhydride was reacted with ethyl p-aminocinnamate and then treated with hydrazine to give 11.3 g (35% yield) of N-[4-(2-ethoxycarbonylvinyl)phenyl]-L-glutamine, m.p. 192.5°–193.3° C.

| Elementary analysis (wt. %) | C | H | N |
| --- | --- | --- | --- |
| Calc. for $C_{16}H_{20}N_2O_5$: | 59.99 | 6.29 | 8.75 |
| Found: | 59.71 | 6.14 | 8.91 |

$[\alpha]_D^{25} = +30.3°$ (c=1 2 N HCl)

Figure 15:
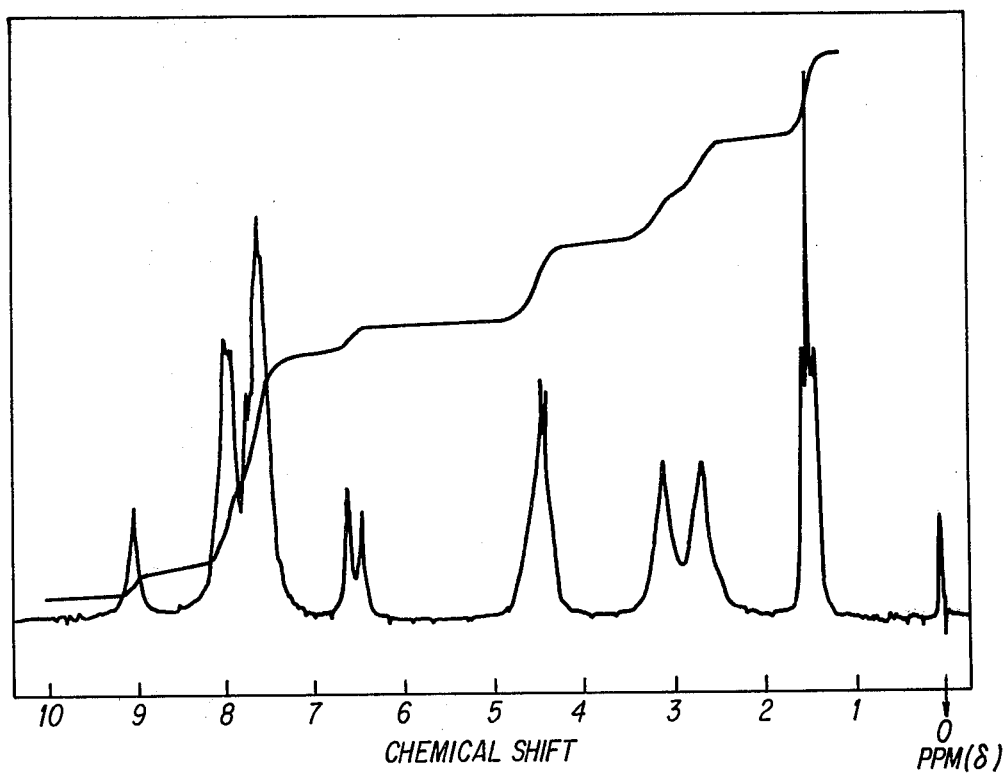
Figure 16:
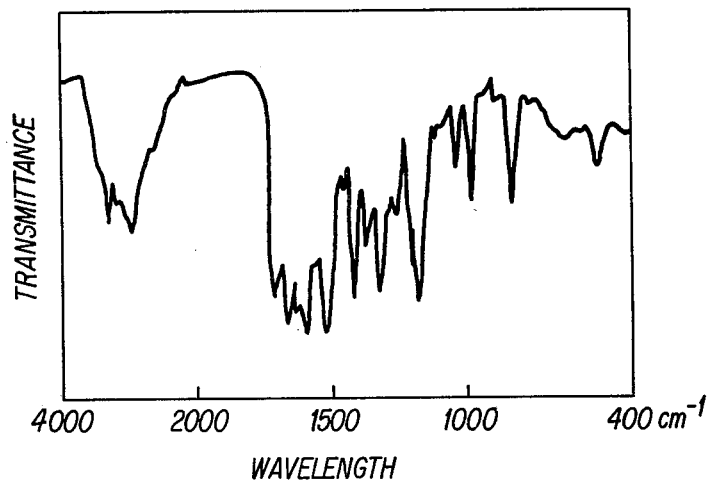

The NMR and IR spectra of the product are shown in FIGS. 15 and 16, respectively.

EXAMPLE 11

N-(4-Ethoxycarbonylmethylphenyl)-L-glutamine: Compound (11) hydrochloride

A mixture of 5.0 g (0.016 mole) of N-(4-ethoxycarbonylmethylphenyl)-L-glutamine in 100 ml of water and 200 ml of ethanol was heated until dissolution was completed and 10 ml of 21 wt. % hydrogen chloride-ethanol solution was added. The solvent was then distilled off in vacuo and the residue was taken up in ethanol. After treatment of the solution with activated charcoal, ether was added thereto for crystallization. The precipitated crystals were sucked off and dried in vacuo to give 2.6 g (0.0075 mole, 47% yield) of N-(4-ethoxycarbonylmethylphenyl)-L-glutamine hydrochloride, m.p. 154.8°–155.6° C.

| Elementary analysis (wt. %) | C | H | N | Cl |
|---|---|---|---|---|
| Calc. for $C_{15}H_{21}N_2O_5Cl_1$: | 52.25 | 6.14 | 8.12 | 10.28 |
| Found: | 54.42 | 5.60 | 7.81 | 10.94 |

EXAMPLE 12

N-(4-Ethoxycarbonylmethylphenyl)-D-glutamine: Compound 12

Following the procedure described in (c) of Example 1, 12.96 g (0.05 mole) of N-phthalyl-D-glutamic acid anhydride was reacted with 8.96 g (0.05 mole) of ethyl p-aminophenylacetate and then treated with hydrazine to give 8.79 g (57% yield) of N-(4-ethoxycarbonylmethylphenyl)-D-glutamine, m.p. 176.2°–177.2° C.

| Elementary analysis (wt. %) | C | H | N |
|---|---|---|---|
| Calc. for $C_{15}H_{20}N_2O_5$: | 58.43 | 6.54 | 9.09 |
| Found: | 58.21 | 6.44 | 9.27 |

$[\alpha]_D^{26} = -28.0°$ (c=1 2 N HCl)

Figure 17:
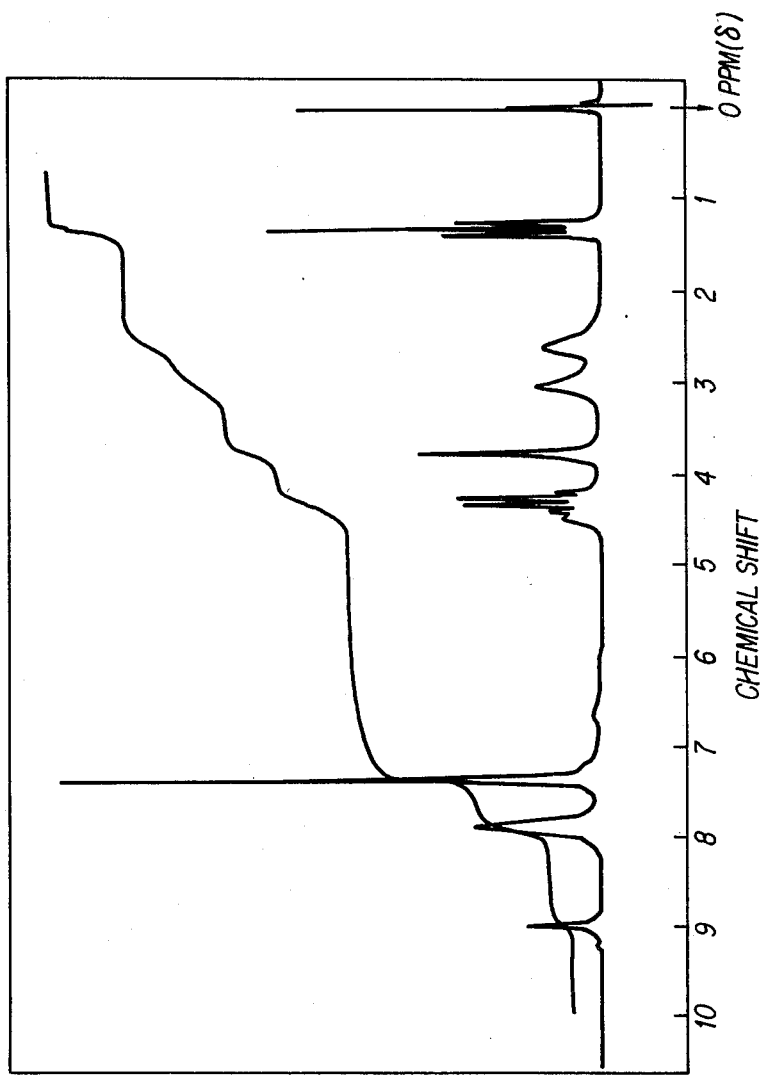
Figure 18:
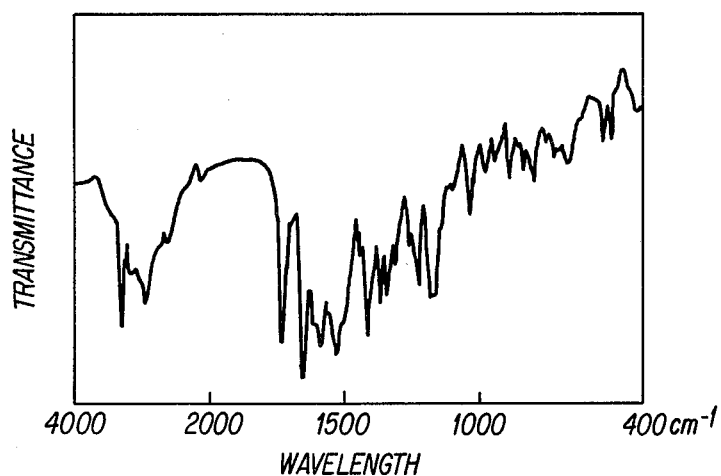

The NMR and IR spectra of the product are shown in FIGS. 17 and 18, respectively.

PREPARATION 2

Ethyl-2-(4-aminophenyl)-n-butyrate

In 100 ml of N,N-dimethylformamide was suspended 11 g of 50% sodium hydride which had been washed with n-hexane and the suspension was stirred under ice cooling. Thereafter, 37.6 g (0.2 mole) of diethyl ethylmalonate was added dropwise thereto and stirring was continued until evolution of hydrogen ceased. Subsequently, a solution of 31.51 g (0.2 mole) of p-chloronitrobenzene in 50 ml of N,N-dimethylformamide was added dropwise. At the end of the dropwise addition, the mixture was heated on an oil bath at 100° C. for 9 hours and N,N-dimethylformamide was distilled off in vacuo. The residue was extracted with ethyl acetate and the ethyl acetate layer was washed with 5% hydrochloric acid and saturated sodium chloride solution and then dried over magnesium sulfate. The ethyl acetate was distilled off in vacuo and the residue was subjected to chromatography on silica gel eluting with a mixture of benzene and n-hexane (1:1) to give 48.64 g (0.157 mole, 79% yield) of diethyl 2-ethyl-2-(4-nitrophenyl)malonate.

In 150 ml of ethanol was dissolved 37.18 g (0.12 mole) of diethyl 2-ethyl-2-(4-nitrophenyl)malonate and a solution of 30.41 g (0.76 mole) of sodium hydroxide in 100 ml of water was added and then heated under reflux for 3 hours on an oil bath. After the solvent was distilled off in vacuo, the residue was dissolved in 200 ml of water and then extracted with 300 ml of ether. The ether layer was removed and the water layer was acidified with conc. hydrochloric acid and extracted again with ether. The ether layer was separated, washed with saturated sodium chloride solution and dried over magnesium sulfate. The ether was distilled off in vacuo to give 17.25 g (0.083 mole, 69% yield) of 2-(4-nitrophenyl)-n-butyric acid.

In 250 ml of ethanol was dissolved 16.71 g (0.08 mole) of 2-(4-nitrophenyl)-n-butyric acid and 15 ml of conc. sulfuric acid was then added and heated under reflux for 3.5 hours on an oil bath. After the ethanol was distilled off in vacuo, the residue was neutralized with saturated sodium bicarbonate solution and extracted with ethyl acetate. The ethyl acetate layer was washed with saturated sodium chloride solution and dried over sodium sulfate. After the ethyl acetate was distilled off in vacuo, the residue was subjected to silica gel chromatography eluting with a mixture of benzene and n-hexane (1:1) to give 9.13 g (0.0385 mole, 48% yield) of ethyl 2-(4-nitrophenyl)-n-butyrate.

A solution of 9.13 g (0.0385 mole) of ethyl 2-(4-nitrophenyl)-n-butyrate in 150 ml of ethanol was subjected to hydrogenation in the presence of palladium black catalyst to give 7.51 g (0.0363 mole, 94% yield) of ethyl 2-(4-aminophenyl)-n-butyrate.

PREPARATION 3

Ethyl 2-(4-aminophenyl)propionate

Following the procedure described in Preparation 2, 35.28 g (0.1196 mole) of diethyl 2-methyl-2-(4-nitrophenyl)malonate was obtained from 25.0 g (0.159 mole) of p-chloronitrobenzene and 29.08 g (0.167 mole) of diethyl methylmalonate (75% yield), and this intermediate was then subjected to hydrolysis, decarboxylation, esterification with ethanol-sulfuric acid and reduction with palladium catalyst in the same way as in Preparation 2 to give 7.86 g (0.041 mole, 26% yield) of ethyl 2-(4-aminophenyl)propionate.

PREPARATION 4

Ethyl 2-(4-aminophenyl)-2-methylpropionate

In 100 ml of N,N-dimethylformamide was suspended 10.56 g (equivalent to 0.22 mole) of 50% sodium hydride which had been washed with n-hexane and the suspension was stirred under ice cooling. A solution of 20.9 g (0.1 mole) of ethyl 4-nitrophenylacetate in 100 ml of N,N-dimethylformamide was then added dropwise and stirring was continued for 1 hour under ice cooling and for 2 hours at room temperature. After the N,N-dimethylformamide was distilled off in vacuo, the residue was extracted with ethyl acetate and the ethyl acetate layer was washed with 5% hydrochloric acid and saturated sodium chloride solution and dried over sodium sulfate. The ethyl acetate was then distilled off in vacuo to give 20.33 g (0.086 mole, 86% yield) of ethyl 2-methyl-2-(4-nitrophenyl)propionate.

In 120 ml of ethanol, 20.33 g of the ester obtained above was hydrogenated with 0.3 g of palladium black catalyst. The palladium catalyst was filtered off and the ethanol was distilled off in vacuo. The residue was taken up in 5% hydrochloric acid and washed with ethyl acetate. The separated water layer was neutralized with sodium carbonate and extracted with ethyl acetate. After the ethyl acetate layer was dried over sodium sulfate, the ethyl acetate was distilled off in vacuo and the residue was subjected to silica gel chromatography using chloroform as a solvent to give 8.31 g (0.04 mole, 47% yield) of ethyl 2-(4-aminophenyl)-2-methylpropionate.

EXAMPLE 13

N-[4-(1-Ethoxycarbonyl-n-propyl)phenyl]-L-glutamine: Compound (13)

To 150 ml of tetrahydrofuran were added 13.23 g (0.0357 mole) of N-carbobenzoxy-L-glutamic acid α-benzyl ester and 5 ml of triethylamine and the mixture was stirred under ice cooling. After 4.7 ml of isobutyl chlorocarbonate was added dropwise, the mixture was stirred under ice cooling for another 30 minutes. A solution of 7.38 g (0.0357 mole) of ethyl 2-(4-aminophenyl)butyrate in 10 ml of tetrahydrofuran was then added dropwise and stirring was continued for 1 hour under ice cooling and for 18 hours at room temperature. After the tetrahydrofuran was distilled off in vacuo, the residue was extracted with ethyl acetate and the ethyl acetate layer was washed with saturated sodium bicarbonate solution, 5% hydrochloric acid and saturated sodium chloride solution and then dried over sodium sulfate. The ethyl acetate was distilled off in vacuo and the residue was recrystallized from ethyl acetate-n-hexane to give 12.99 g (0.0232 mole, 65% yield) of an intermediate.

This intermediate (12.99 g) was dissolved in 200 ml of ethanol and hydrogenated with addition of 0.3 g of palladium black. The palladium catalyst was then filtered off and the ethanol was distilled off in vacuo. The residue was recrystallized from ethanol-water to give 4.59 g (0.0136 mole, 38% yield) of N-[4-(1-ethoxycarbonyl-n-propyl)phenyl]-L-glutamine, m.p. 156.8°–157.0° C.

| Elementary analysis | C | H | N |
|---|---|---|---|
| Calc. for $C_{17}H_{24}N_2O_5$: | 60.70 | 7.19 | 8.33 |
| Found: | 60.42 | 7.07 | 8.45 |

$[\alpha]_D^{27°} = +25.0°$ (2 N-HCl)

Figure 19:
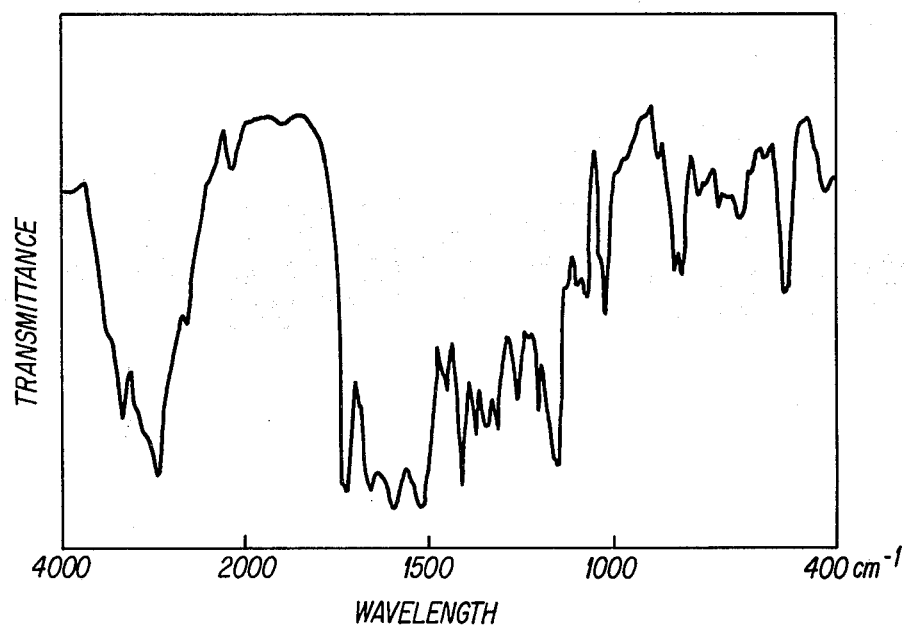
Figure 20:
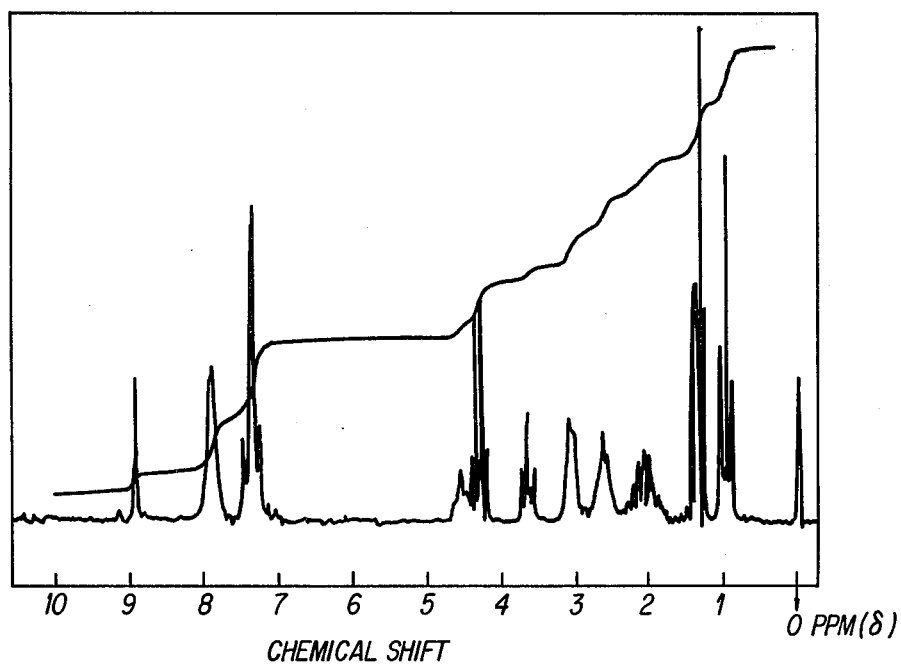

The IR spectrum (KBr) and NMR spectrum ($CF_3COOH$) are shown in FIGS. 19 and 20, respectively.

EXAMPLE 14

N-[4-(1-Ethoxycarbonyl-1-methylethyl)phenyl]-L-glutamine: Compound (14)

Following the procedure described in Example 13, 4.84 g (0.0086 mole) of an intermediate was obtained from 5.91 g (0.0159 mole) of N-carbobenzoxy-L-glutamic acid α-benzyl ester and 3.3 g (0.0159 mole) of ethyl 2-methyl-2-(4-aminophenyl)propionate (54% yield), and it was hydrogenated with palladium black catalyst in the same manner as in Example 13 to give 1.05 g (0.0031 mole, 36% yield) of N-[4-(1-ethoxycarbonyl-1-methylethyl)phenyl]-L-glutamine, m.p. 146.6°–148.5° C.

| Elementary analysis | C | H | N |
|---|---|---|---|
| Calc. for $C_{17}H_{24}N_2O_5$: | 60.70 | 7.19 | 8.33 |
| Found: | 60.40 | 6.60 | 8.59 |

$[\alpha]_D^{27°} = +25.7°$ (2 N-HCl)

Figure 21:
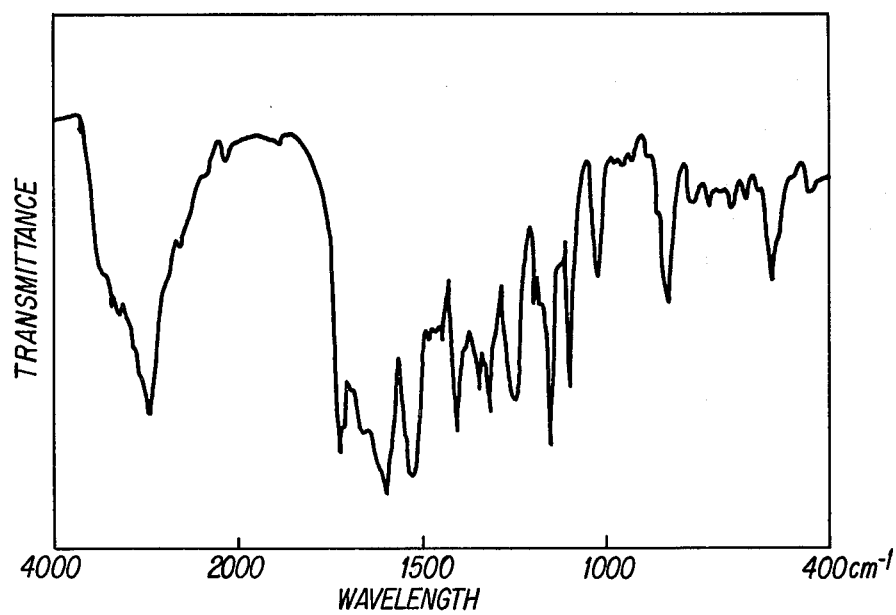

The IR spectrum (KBr) is shown in FIG. 21.

EXAMPLE 15

N-[4-(1-Ethoxycarbonylethyl)phenyl]-L-glutamine: Compound (15)

Following the procedure described in Example 13, 7.88 g (0.0144 mole) of an intermediate was obtained from 7.13 g (0.0192 mole) of N-carbobenzoxy-L-glutamic acid α-benzyl ester and 4.4 g (0.0192 mole) of ethyl 2-(4-aminophenyl)propionate hydrochloride (75% yield), and it was hydrogenated with palladium black catalyst in the same manner as in Example 13 to give 2.7 g (0.0084 mole, 44% yield) of N-[4-(1-ethoxycarbonylethyl)phenyl]-L-glutamine, m.p. 157.4°–157.9° C.

| Elementary analysis | C | H | N |
|---|---|---|---|
| Calc. for $C_{16}H_{22}N_2O_5$: | 59.62 | 6.88 | 8.69 |
| Found: | 59.31 | 6.86 | 8.57 |

$[\alpha]_D^{27°} = +27.9°$ (2 N HCl)

Figure 22:
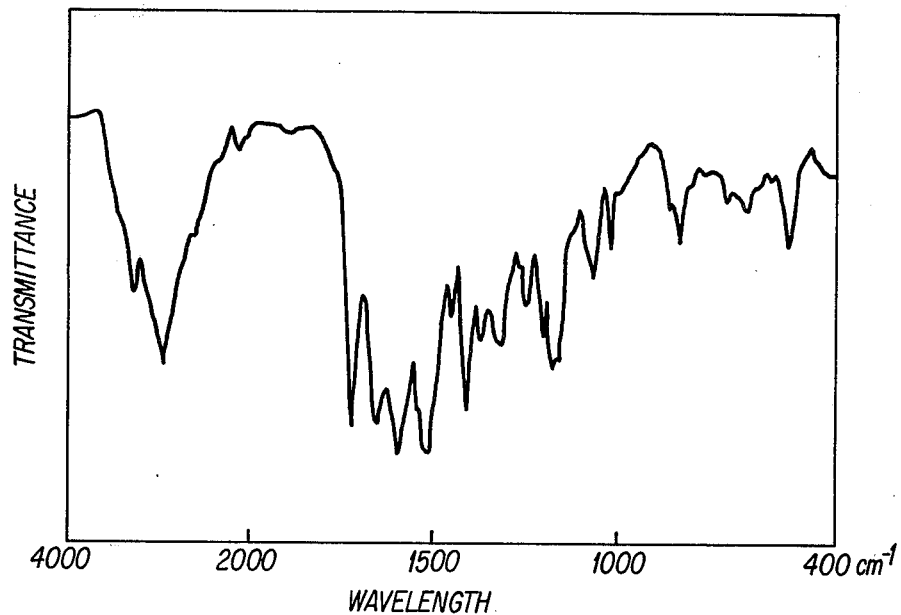

The IR spectrum (KBr) is shown in FIG. 22.

EXAMPLE 16

N-[4-(1-Carboxy-n-propyl)phenyl]-L-glutamine: Compound (16)

In 10 ml of methanol was suspended 1.68 g (0.005 mole) of N-[4-(1-ethoxycarbonyl-n-propyl)phenyl]-L-glutamine and a solution of 0.42 g of sodium hydroxide in 20 ml of water was added thereto and stirred for 1.5 hours at room temperature. The solvent was then distilled off in vacuo to about a half volume and the remaining solution was acidified to pH 4 with 5% hydrochloric acid. The precipitated crystals were collected by filtration, washed with cold water and dried in vacuo to give 1.16 g (0.0038 mole, 75% yield) of N-[4-(1-carboxy-n-propyl)phenyl]-L-glutamine, m.p. 166.5°–167.0° C.

| Elementary analysis | C | H | N |
|---|---|---|---|
| Calc. for $C_{15}H_{20}N_2O_5$: | 58.43 | 6.54 | 9.09 |
| Found: | 57.67 | 6.33 | 9.00 |

$[\alpha]_D^{27°} = +24.0°$ (2 N-HCl)

Figure 23:
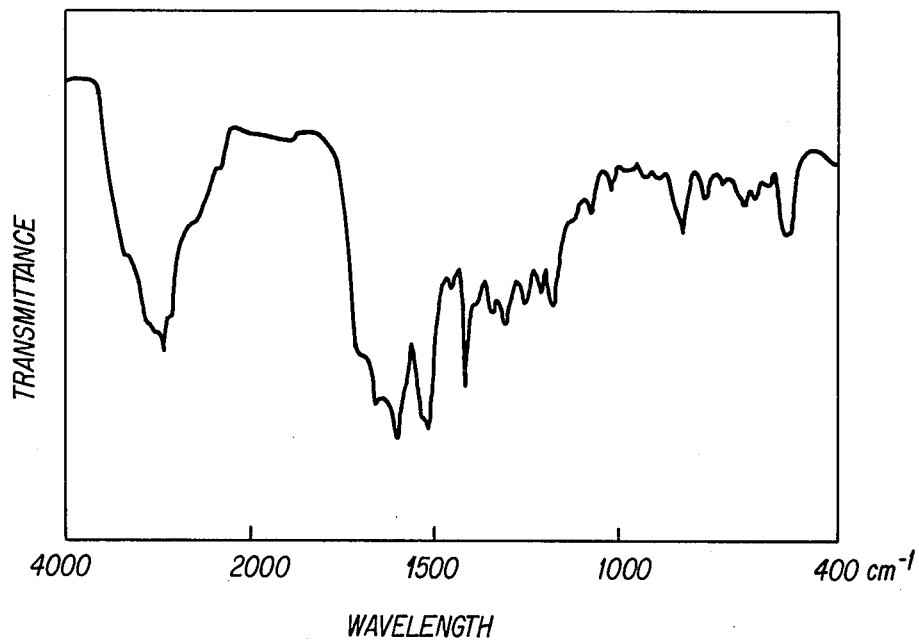

The IR spectrum (KBr) is shown in FIG 23.

TEST 1 ACUTE TOXICITY

The test drug was suspended in aqueous 50% solution of Tween 80 and administered to ddY mice weighing 20–25 g orally or intraperitoneally in doses indicated in Table 1 below. The number of medicated mice that died during 7 days after the administration is shown in Table 1.

TABLE 1

| Drug | Dose (mg/kg) | Route | No. of dead mice/ No. of test animals |
|---|---|---|---|
| Compound (1) | 1,000 | IP | 0/5 |
|  | 5,000 | PO | 0/5 |
| Compound (2) | 1,000 | IP | 0/5 |
|  | 5,000 | PO | 0/5 |
| Compound (13) | 1,000 | IP | 0/5 |
|  | 5,000 | PO | 0/5 |

TEST 2 EFFECT ON PLAQUE FORMING CELLS IN THE SPLEEN OF MICE WHEN INOCULATED WITH SHEEP RED BLOOD CELLS

Mice were inoculated by intravascular or intraperitoneal administration of $1 \times 10^8$ sheep cells per animal. Each group consisted of five mice. The test drug was administered orally or intraperitoneally for four consecutive days from the day when the sheep cells were administered. Four days later, the mice were sacrificed and the number of plaque forming cells (PFC) in the spleen based on the sheep red blood cells was determined according to the Fujiwara et al. method ["Procedure of Immune Experiments", Vol. 5, p. 1475, Japan, (1976)] which is a modification of the Canninghum method.

The results are shown in Table 2.

TABLE 2

| Run No. | Strain of mouse | Weekly age | Immunization route of sheep cells | Drug | Dose (mg/kg) | Route | PFC × 2,500/spleen (Mean ± standard error) |
|---|---|---|---|---|---|---|---|
| 1 | Balb/c | 4 | Intravascular | Physiological saline | — | P.O. | 81.4 ± 6.16 |
| " | " | " | " | Azathioprine | 50 | " | 22.8 ± 2.40 |
| " | " | " | " | Compound (2) | 30 | " | 99.0 ± 4.60 |
| " | " | " | " | " | 100 | " | 91.8 ± 18.6 |
| " | " | " | " | " | 300 | " | 73.4 ± 12.7 |
| 2 | C3H/He | 7 | I.P. | Physiological saline | — | P.O. | 76.5 ± 26.3 |
| " | " | " | " | Azathioprine | 50 | " | 46.7 ± 1.2 |
| " | " | " | " | Compound (2) | 30 | " | 113.0 ± 20.4 |
| " | " | " | " | " | 100 | " | 160.0 ± 20.6 |
| " | " | " | " | " | 300 | " | 152.4 ± 11.4 |

TEST 3 EFFECTS ON DELAYED HYPERSENSITIBITY

Into the palms of the right rear limbs of mice (ddY strain, weighing 25-30 g) was injected 40 μl of sheep red blood cells the concentration of which was adjusted to $1 \times 10^7/40$ μl. The test drug was administered intraperitoneally or orally for four consecutive days inclusive of the day of sheep red blood cell administration.

Three days after the day of sheep red blood cell administration, 40 μl of sheep red blood cells which were adjusted to have a concentration of $5 \times 10^8/40$ μl were administered into the palms of the left rear limbs.

After 24 hours, the thickness of the palms of the right and left rear limbs was measured. The edema was expressed as the difference in thickness between the palms of the left and right rear limbs. The results are shown in FIG. 3, in which the edema in the medicated group is expressed as percent control which means the percentage of the edema found in the group in which physiological saline is applied (control group).

TABLE 3

| Drug | Dose (mg/kg) | Route | % Control |
|---|---|---|---|
| Compound (1) | 3 | I.P. | 85.2 |
| | 10 | " | 78.2 |
| | 30 | " | 91.7 |
| | 30 | P.O. | 85.7 |
| | 100 | " | 76.4 |
| | 300 | " | 74.5 |
| Compound (2) | 3 | I.P. | 69.7 |
| | 10 | " | 65.9 |
| | 30 | " | 62.3 |
| | 30 | P.O. | 78.8 |
| | 100 | " | 66.2 |
| | 300 | " | 65.0 |
| Compound (4) | 3 | I.P. | 70.4 |
| | 10 | " | 80.2 |
| | 30 | " | 91.7 |
| | 30 | P.O. | 91.7 |
| | 100 | " | 91.9 |
| | 300 | " | 79.6 |
| Compound (5) | 3 | I.P. | 91.6 |
| | 10 | " | 95.7 |
| | 30 | " | 72.2 |
| | 30 | P.O. | 94.5 |
| | 100 | " | 84.7 |
| | 300 | " | 82.2 |
| Compound (6) | 3 | I.P. | 94.6 |
| | 10 | " | 83.2 |
| | 30 | " | 84.3 |
| | 30 | P.O. | 81.1 |
| | 100 | " | 82.8 |
| | 300 | " | 83.1 |
| Compound (7) | 3 | I.P. | 92.4 |
| | 10 | " | 91.1 |
| | 30 | " | 86.8 |
| | 30 | P.O. | 92.8 |
| | 100 | " | 84.8 |
| | 300 | " | 82.3 |
| Compound (8) | 3 | I.P. | 76.2 |
| | 10 | " | 76.7 |
| | 30 | " | 81.0 |
| | 30 | P.O. | 85.0 |
| | 100 | " | 80.6 |
| | 300 | " | 92.3 |
| Compound (9) | 3 | I.P. | 91.3 |
| | 10 | " | 80.2 |
| | 30 | " | 100.6 |
| | 30 | P.O. | 85.3 |
| | 100 | " | 96.7 |
| | 300 | " | 88.9 |
| Compound (10) | 3 | I.P. | 100 |
| | 10 | " | 101 |
| | 30 | " | 85.8 |
| | 30 | P.O. | 81.3 |
| | 100 | " | 109.9 |
| | 300 | " | 82.6 |
| Compound (11) | 3 | I.P. | 77.7 |
| | 10 | " | 67.3 |
| | 30 | " | 84.1 |
| | 30 | P.O. | 89.8 |
| | 100 | " | 80.8 |
| | 300 | " | 83.7 |
| Hydrochloride Compound (2) | 3 | I.P. | 79.6 |
| | 10 | " | 90.7 |
| | 30 | " | 90.0 |
| | 30 | P.O. | 81.8 |
| | 100 | " | 75.7 |
| | 300 | " | 67.2 |
| Compound (12) | 3 | I.P. | 76.1 |
| | 10 | " | 107.9 |
| | 30 | " | 89.1 |
| | 30 | P.O. | 85.4 |
| | 100 | " | 81.7 |
| | 300 | " | 80.7 |
| Compound (15) | 3 | I.P. | 78.0 |

TABLE 3-continued

| Drug | Dose (mg/kg) | Route | % Control |
|---|---|---|---|
| | 10 | " | 62.6 |
| | 30 | " | 67.6 |
| Compound (14) | 3 | I.P. | 77.3 |
| | 10 | " | 72.6 |
| | 30 | " | 71.9 |
| Compound (13) | 3 | I.P. | 82.1 |
| | 10 | " | 70.5 |
| | 30 | " | 64.2 |
| Compound (13) | 30 | P.O. | 89.6 |
| | 100 | " | 87.4 |
| | 300 | " | 75.7 |
| Azathioprine | 30 | I.P. | 61.0 |
| | 100 | P.O. | 58.2 |

TEST 4 EFFECT ON RAT ADJUVANT ARTHRITIS

Test Method

The test animals were Sprague-Dawley rats at the age of 8 weeks and each group consisted of ten animals. An intracutaneous injection of 0.05 ml of a suspension of 0.5 mg of *Mycobacterium butyricum* in liquid paraffin was applied to each animal at the paw of the right rear limb. For 27 consecutive days from the day before the adjuvant injection, Compound (2) was orally administered at doses of 3, 10 and 30 mg/kg with measurement of the volume of the paw.

RESULTS

About 10 days after the adjuvant injection, so-called secondary inflammations were developed. They were observed as swelling in the injected and non-injected limbs and tubercles in the ear, tail, limbs and the like. Compound (2) exerted an inhibitory action on these secondary inflammations in every dose. However, any definite dose dependency was not appreciated. In the rats affected with adjuvant arthritis, the development of secondary inflammations was accompanied by a decrease in body weight. With respect to the decrease in body weight an improving tendency, was noted in the group to which Compound (2) was applied.

The inhibitory action of Compound (2) on primary inflammations caused by direct reaction of the adjuvant was very slight. Having now fully described the invention, it will be apparent to one of ordinary skill in the art that many changes and modifications can be made thereto without departing from the spirit of the invention as set forth herein.

What is claimed is:

1. Glutamine derivative of the formula:

wherein X is (i) an alkylene of the formula: $(-CH_2-)_n$ where n is an integer of 1 to 4, or vinylene, or (ii) a group of the formula:

$$\begin{array}{c} R^2 \\ | \\ -C- \\ | \\ R^1 \end{array}$$

where $R^1$ and $R^2$ may be the same or different and are hydrogen or a lower alkyl with the proviso that at least one of $R^1$ and $R^2$ is a lower alkyl; and Z is hydrogen or a lower alkyl or a nontoxic salt thereof.

2. The compound according to claim 1 wherein Z is hydrogen.

3. The compound according to claim 1 wherein Z is a lower alkyl.

4. A method of modulating immune reaction in a disease which comprises administering an effective dosage of a compound represented by the formula (I) as described in claim 1.

5. The method of claim 4, wherein said disease is rheumatoid arthritis, systemic lupus erythematodes, collagen disease, asthma, cancer or bacterial infectious disease.

6. An immunomodulating composition comprising an effective amount of at least one compound represented by the formula (I) as described in claim 1 and at least one non-toxic carrier.

7. The method of claim 4 wherein said dosage is about 0.1 mg to 1,000 mg per kilogram of body weight.

* * * * *